United States Patent [19]

Dunford

[11] Patent Number: 4,670,911
[45] Date of Patent: Jun. 9, 1987

[54] ATTACHABLE EAR COVERING FOR SPORT ACTIVITIES

[75] Inventor: Scott V. Dunford, Salt Lake City, Utah

[73] Assignee: Skiears, Inc., Salt Lake City, Utah

[21] Appl. No.: 911,782

[22] Filed: Sep. 26, 1986

[51] Int. Cl.$^4$ ............................................. A41D 13/00
[52] U.S. Cl. ............................................. 2/209; 2/423
[58] Field of Search .............................. 2/9, 209, 423

[56] References Cited

U.S. PATENT DOCUMENTS

| | | | |
|---|---|---|---|
| 863,315 | 8/1907 | Pierce | 2/423 |
| 1,468,556 | 9/1923 | Camp et al. | 2/423 |
| 1,621,629 | 3/1927 | Dawson | 2/448 |
| 2,593,892 | 4/1952 | Kindel | 2/6 X |
| 2,609,544 | 9/1952 | Berg | 2/209 |
| 2,693,599 | 11/1954 | Berg | 2/209 |
| 2,861,270 | 11/1958 | McCoy | 2/423 |
| 3,249,949 | 5/1966 | Rosenberg | 2/209 |
| 3,378,851 | 4/1968 | McBrayer | 2/454 |
| 3,823,713 | 7/1974 | Shah | 2/209 X |
| 3,943,574 | 3/1976 | Yamaguchi | 2/9 |

*Primary Examiner*—Louis K. Rimrodt
*Attorney, Agent, or Firm*—Thorpe, North & Western

[57] ABSTRACT

An ear protection device for attachment to support structure for eyeware such as ski goggles or glasses and being useful to keep ears warm and protected from adverse weather conditions. The ear protection device comprises a support member which includes an opening positioned within the support member for placement at the ear and a covering member which is attachable to the support member and includes a shell which provides an exterior enclosure for the ear when in a folded and closed configuration with the support member.

13 Claims, 8 Drawing Figures

ATTACHABLE EAR COVERING FOR SPORT ACTIVITIES

BACKGROUND OF THE INVENTION

1. Field of Invention

This invention relates to a protective ear covering which may be attached and suspended from the head-strap of ski goggles or to the retaining arms of eye glasses. More particularly, the present invention relates to protective ear coverings which fold around the strap or eye glass structure and which are coupled directly or indirectly to the ear.

2. Prior Art

Protection of ears from cold weather has been accomplished by a variety of devices. U.S. Pat. No. 2,693,559 discloses one example of an ear muff device which comprises a pair of ear coverings supported on a head band. This and similar types of ear muff devices utilize the top of the head to support a flexible band which permits the ear muffs to hang down and position over the ears. This is in contrast with U.S. Pat No. 1,468,556 which suggests that the ear covering be attached directly to the ear. It is apparent from this latter patent that the design is not adapted for protecting the ear against cold temperatures, but rather merely protecting against object intrusion or sound. In a similar manner, U.S. Pat. No. 1,621,629 discloses a protective covering which can be attached to a support arm of safety goggles. Again, the covering is not adapted for protection against cold temperatures.

U.S. Pat. No. 2,333,392 discloses an ear covering which is suspended from the support structure of a hat band. U.S. Pat. No. 2,593,892 discloses another form of ear covering which is designed to prevent access of water such as occurs in a swimming pool. Finally, U.S. Pat. No. 3,823,713 discloses a unique configuration for an ear covering for medical purposes. It is attached directly to the ear and does not involve the use of support structure.

Although the referenced prior art gives general assistance in providing protective earware for general circumstances, it is not particularly useful for specific applications. For example, protecting ears from cold temperatures in extreme conditions such as are experienced in skiing presents unique problems which are not addressed by the prior art. Such an environment requires a very strong attachment to the ears in order to withstand the abrupt and sometimes severe movement experienced by the body as it traverses difficult skiing terrain. Such special requirements are illustrated in U.S. Pat. No. 3,943,574 which discloses a combination ear covering and face mask. Here again, the ear covering is supported by an overhead strap which positions and supports the face mask and ear covering. It is apparent from this disclosure that the apparatus is bulky and must typically be either worn over the face and ears, or stored separate from the person.

What is needed is a more portable and adaptable form of ear covering which can be used in combination with conventional equipment such as ski goggles or glasses, but which can be stored and carried on the person without difficulty. It would also be helpful to have an improved form of ear covering which provides comfort beyond the conventional head band which is disposed around the head, over the forehead and which covers the ears. Such an ear covering could eliminate the use of bulky stocking caps and other extreme cold head gear and would suffice to meet the protection needs in mild weather.

OBJECTS AND SUMMARY OF THE INVENTION

It is therefore an object of the present invention to provide a form of ear covering which is attachable directly to the elastic band of ski goggles or to the side support arms of glasses.

It is a further object of this invention to provide such an ear covering which may be suspended from the goggles or glasses and may be positioned over or around the ear to fully protect it from cold weather.

An additional object of this invention is to provide such structure which is easily removed and stored in a pocket or other small location and which permits quick change as weather conditions vary.

A still further object of this invention is to provide an ear covering which contributes to the style and fashion of ski wear.

A still further object of this invention is to provide a decorative ear covering which is adaptable for use with other sport activities and which can support or contain ear phones for use with a radio or tape player.

These and other objects are realized in an ear protective device for attachment around lateral support structure for earware such as ski goggles or glasses. The device comprises a flexible support member having a central opening for positioning against the ear or which may be sufficiently large to permit the ear to pass through while providing a comfortable fit around the ear in position against the wearer's head. The central opening is formed by a substantially circumscribing body which has a first side positioned against the head and ear and a second side disposed in the opposite direction. The configuration of the support member extends beyond the circumference of the ear to be covered. A covering member is attachable to the support member and is large enough to provide an exterior enclosure for the ear. The support member and covering member are coupled together in an enclosing relationship with respect to the referenced lateral support structure such as the head band of ski goggles. Accordingly, the device is supported at the ear by suspension around the support structure of the eyeware, and may also be supported by direct attachment to the ear.

DETAILED DESCRIPTION OF THE INVENTION

Figure 2:
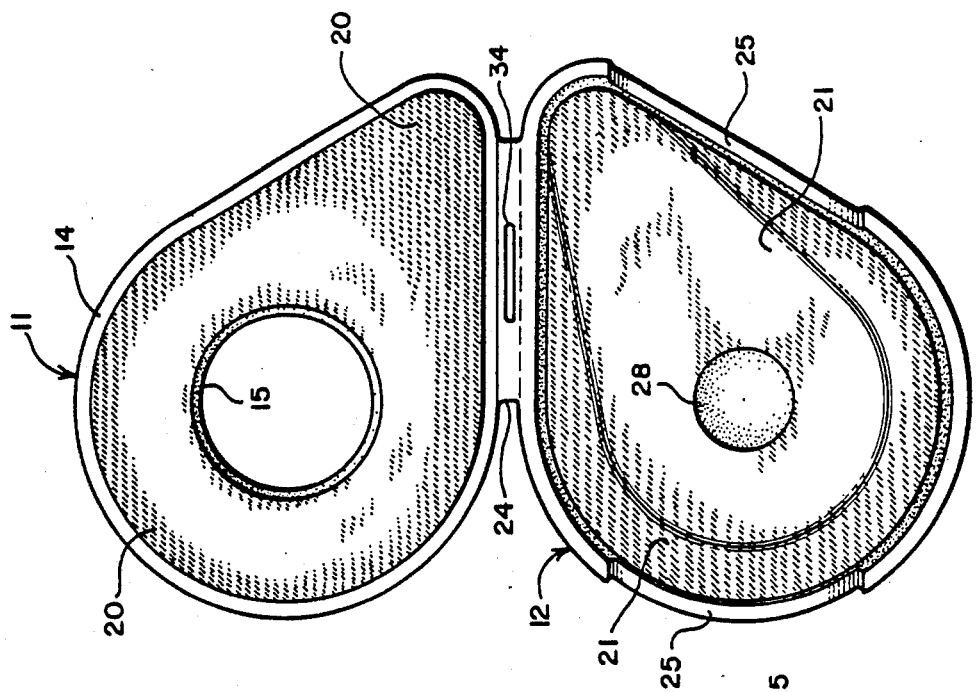
FIG. 2 is a plan view of the subject device in open configuration, showing the opposite side as compared with FIG. 1.
Figure 6:
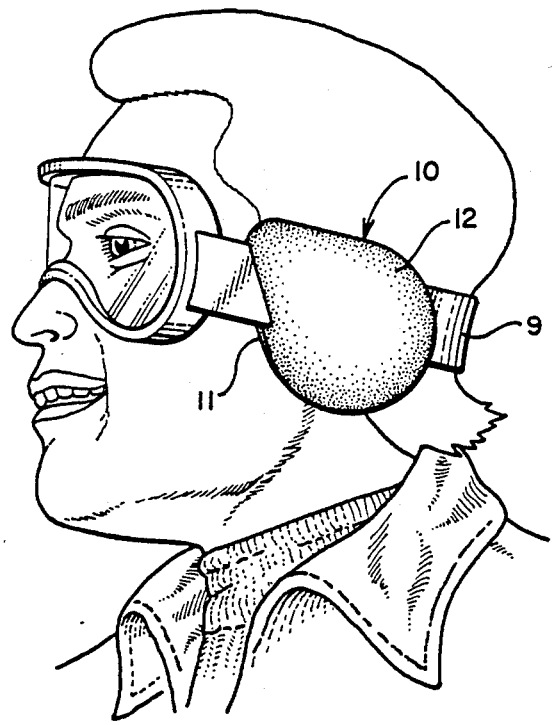
FIG. 6 illustrates the subject ear protective device in position around the head strap of ski goggles.

Referring now to the drawings:

A preferred embodiment of the ear protective device described herein is shown as item 10 in FIG. 6 in a supported position around the head strap 9 for ski goggles. The device could also be mounted to the side support arms of glasses, or in similar manner to other types of protective eye wear.

The device is comprised of a support member 11 and a covering member 12 which are hinged or otherwise attached to enable the closure of the support member 11 against the covering member 12 about the strap 9 of the ski goggles. The ear of the wearer is protected within a contained area between the head and these respective members 11 and 12. Accordingly, the device keeps the ear warm and covered, and with proper selection of material has little interference with the hearing of the individual.

Figure 1:
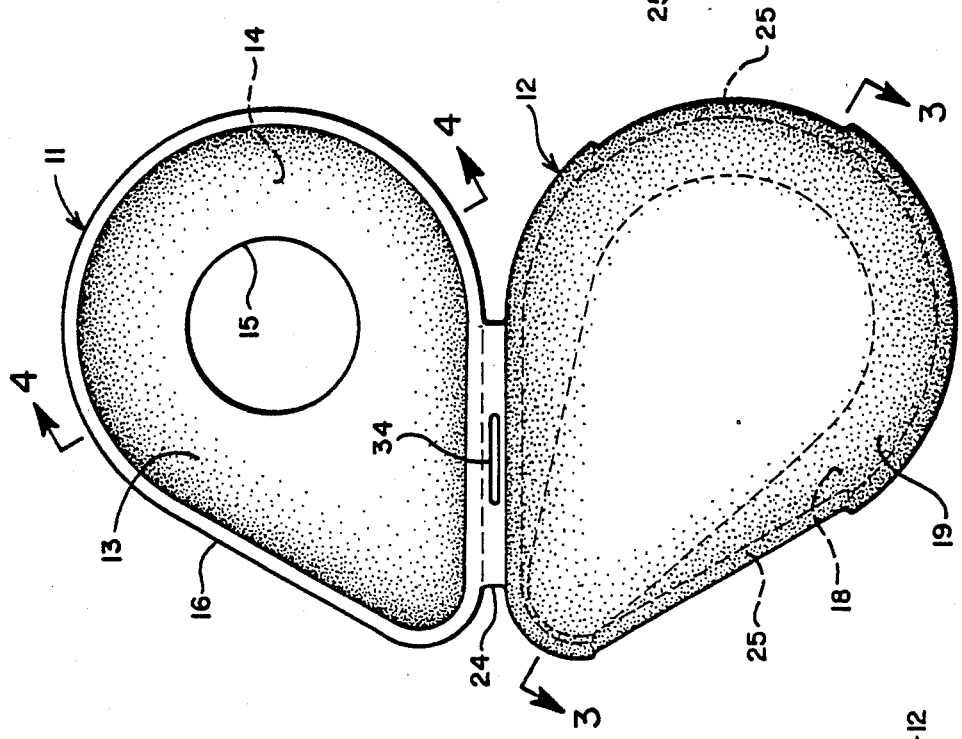
FIG. 1 is a plan view of one side of the subject ear protection device in an open configuration.

FIGS. 1 through 5 present a variety of views of the subject device which better enable a detailed explanation of its structure and function. For example, FIG. 1 shows the ear protective device in an open configuration. Its two principle components are again shown as items 11 and 12 generally. Item 11 comprises a support member having a first side 13 in open view in the drawing, the back side or second side 14 being disposed in a concealed position as shown by the phantom line representation. The first side which is viewed directly in FIG. 1 is actually disposed against the head or against the ear of the wearer, with the second side oriented away from the head and adapted for attachment of the covering member 12 thereto.

The support member 11 includes a central opening 15 which gives access to a cavity of air space contained within the mated device. The opening can alternatively be designed sufficiently large to permit the ear of the wearer to pass therethrough and yet sufficiently small to provide a comfortable fit around the ear when positioned against the wearer's head. For ear protective devices adapted for adults, this opening size will range from 2 centimeters to 7 centimeters. Although the drawings show a circular configuration, it will be apparent that an elliptical shape or other opening construction may be equally acceptable. The primary function of this opening is to provide access to the interior cavity with a comfortable fit of the support member and attached covering member at the ear of the wearer.

Surrounding this opening 15 is a substantially circumscribing body which includes the first side 13 and second side 14 previously discussed. This body provides the support to suspend a goggle strap between the attached covering and support members and at the ear of the wearer. The cupped shape of the device is held at the ear by tension applied from the taut straps of the ski goggles.

In the configuration where the support body surrounds the ear, it need not totally surround but should be substantially circumscribing to provide sufficient support so that the ear assists to retain this support member in proper position. The full, annular configuration shown in the drawings provides a preferred structure because it allows the support member to be slightly stretched around the ear when this member is constructed of flexible, elastic material. Typical construction materials include polyethers such as Devalite (TM) EVA Foam. These materials provide the desired flexibility and elastic properties which facilitate comfortable placement of the support member around the ear. Typically, these materials will be foamed to provide light weight and improved insulation properties.

The second member 12 functions as a covering to enclose the ear between its interior surface 18 and the wearers head. In essence, the covering member operates as a shell which provides exterior enclosure to the ear when attached to the support member in a closed, contiguous relationship as shown in FIG. 6. Therefore, the covering member will typically be slightly larger than the support member and will be fabricated with a comparable geometric configuration and perimeter which conforms to the shape of the head around the ear and adapts the respective covering and support members to be coupled together to form an enclosure for the protected ear. It is the covering member which provides the primary protection and comfort against cold temperatures and other adverse weather conditions such as snow or rain. In addition, the exterior surface 19 of the covering member may include design features which enhance the aesthetic appearance of the protection device and provide an aspect of fashion to the wearer.

As shown in the drawings, a preferred configuration for these respective members 11 and 12 is a mating convex, concave construction. In this embodiment, the first side 13 of the circumscribing body 16 and the interior surface 18 of the covering member 12 are concave with respect to the wearer's head. The second side 14 of the support member 11 and the exterior face 19 of the covering member are convex, adapting the structure to be nested about the ear in a closed configuration. Specifically, the second side 14 of the support member being configured to nest at the interior surface 18 of the covering member 12. These concave and convex configurations are better shown in FIGS. 3 and 4. The nesting relationship of the support member 11 within the covering member 12 is better shown in FIG. 5. As has been previously noted the ear may also be positioned at the interior side 13.

The means for attaching the covering member 12 to the support member 11 is best shown in FIG. 2. This attachment means comprises a material such as Velcro (trademark) 20 adhered to the second side of the support member 11. The Velcro material is cut to a similar to that shape shown for item 20, including the central opening 15 which allows passage of the ear therethrough. A mating sheet of Velcro material 21 is adhered to the interior 18 of the covering member in a juxtaposed position with the first sheet, the respective sheets of Velcro material being thereby adapted to adhere upon closure of the respective members 11 and 12. It will be apparent that either the tooth or hoop side of the Velcro material can be applied in alternate manner to the respective support and covering members 11 and 12, or that other fastening type materials may similarly be utilized.

Figure 5:
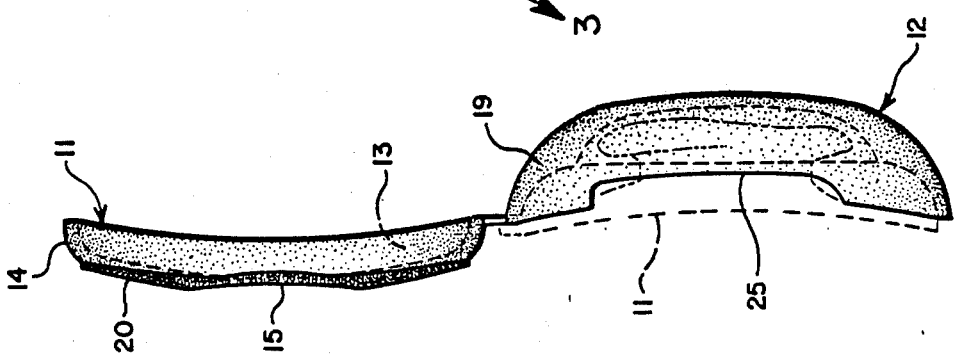
FIG. 5 is a side view along the plane of the device as shown in FIG. 1, viewed from the left side of the figure, and showing the device in a closed configuration (phantom line embodiment).

To facilitate proper alignment upon closure and to retain the respective members 11 and 12 in an attached relationship to avoid loss of one member from the other, a hinge member 24 is coupled between the support member 11 and covering member 12. This additional attachment means is coupled at the edges of the respective support and covering members to allow the members to be folded into a closed, nested configuration as previously discussed, and as shown in FIGS. 5 and 6. This hinge member may be formed as an integral part of either the support member or covering member, or may, more preferably, be formed as an integral part of both the support member and covering member as shown in the drawings. When constructed as a single, integral structure, the subject ear covering device can be easily retained in the pocket of the wearer and may quickly be positioned around the ear and closed to provide the desired ear protection. In fact, both the Velcro and any exterior decorative fabric can be heat sealed to the support and covering members with no need for stitching to form a single, integral structure.

As best shown in FIG. 2, the covering member further includes a ski strap indentation 25 at forward and rearward positions. These forward and rearward indentations 25 form a channel through which the ski goggle strap 9 can pass and which allows the covering member to close over the strap without being deflected away from its closed position. With the indentations properly aligned with the ski strap, the covering member can rest snugly against the support member and further enclose the contained ear. The forward indentation 25 may be used in a similar manner for a channel opening for the support arms of glasses or similar eyewear.

Figure 3:
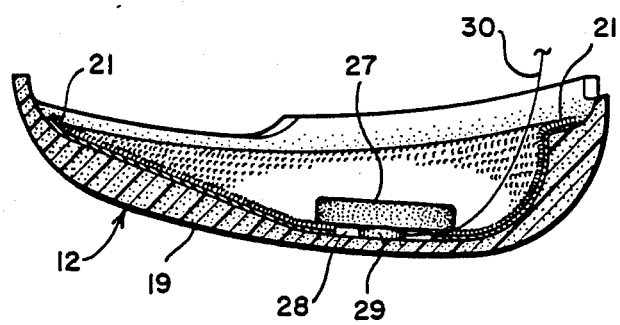
FIG. 3 is a cross-sectional view taken along the lines 3—3 of FIG. 1.
Figure 4:
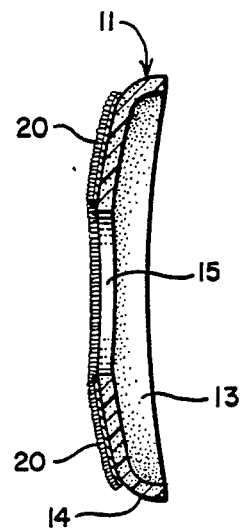
FIG. 4 is a cross-sectional view taken along the lines 4—4 of FIG. 1.

FIG. 3 discloses how an ear speaker 27 may be coupled to the interior surface 18 of the covering member. Where the ear speaker is covered with an open-cell foam, and if the Velcro material 21 applied to the interior surface of the covering member is the tooth side of such Velcro material, the open-cell foam covering will adhere directly to the Velcro. With this use in mind, the Velcro material applied to the interior surface 18 includes a center opening 28 which provides a recess for a back portion 29 of the ear speaker 27. In this manner, the ear speaker is fully contained within the nested support member and covering member. The Velcro 21 can be displaced away from the center of side 18 to create a void space there between, increasing the volume for a speaker. This enclosed configuration for the ear speaker retains it in its appropriate hearing position, despite the worst bumps and movements which occur as the skier traverses rugged terrain. The ear speaker 27 is easily coupled to a tape recorder or radio device by means of conventional hook up wire 30.

Figure 7:
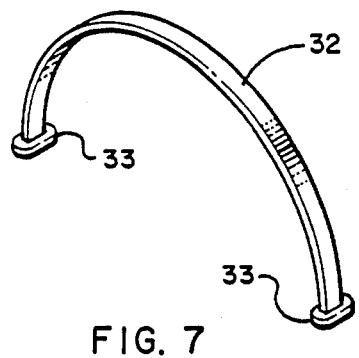
FIG. 7 shows a perspective view of a head support strap useful with the disclosed invention.

The subject ear protection device may further be adapted with head support means to provide additional security and retention force for maintaining the ear protective device in place at the ears. This further support means comprises means positioned at a top portion of the device (when in a closed configuration as shown in FIG. 6) for attachment to an arcuate head support band as illustrated in FIG. 7. This band can be positioned over the top of the head of the wearer and includes a strap portion 32 and a pair of distal disks 33. These disks are adapted to be inserted through slots 34 positioned in the hinge member 24 of the protective ear device. The disks are dimensioned slightly larger than the slots to enable retention thereof. Together, they can be used to secure a pair of ear protective devices in the absence of lateral support structure of ski goggles or glasses, or can supplement the support offered by such goggles or glasses.

Figure 8:
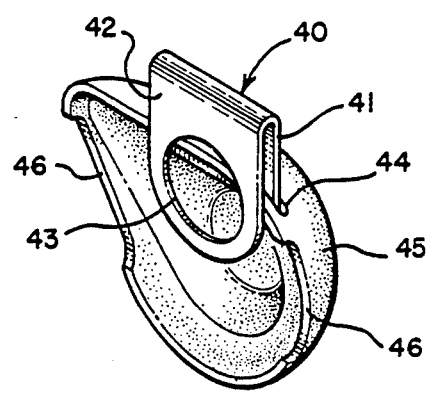
FIG. 8 shows an alternative embodiment of the present invention.

It will be apparent to those skilled in the art that other embodiments can be adapted which incorporate the inventive principles disclosed herein. For example, FIG. 8 discloses an alternative embodiment wherein the support member 40 comprises a channel shaped plastic insert having an ear insert side 41 and a support side 42. A central opening 43 enables the support member to be positioned around the ear of the wearer or between the ear and support strap of ski goggles. Insert side 41 is then inserted tightly into a pocket 44 in a covering member 45. As with the preferred embodiment, forward and rearward indentations 46 allow for passage of a ski goggle strap therethrough. The insertable configuration of the support member 40 within the covering member 45 provides means to join the respective members in the desired enclosing relationship with respect to the ear of the wearer.

The ear protection device as disclosed in the present invention provides numerous advantages over the prior art. It represents a fashionable form of ear covering which facilitates positioning at the ears without disturbing the wearer's particular hair style. It provides comfort without the weight and bulk of typical ear coverings such as stocking caps, ear muffs and the like. It does not cause the typical itch which occurs with a stocking cap over the head of the wearer and which operates to compress a hair style and, perhaps, provide more head protection than is desired. In contrast, the ear covering of the present invention covers only the ears, leaving the rest of the head and face free to breath normally. When the outer covering extends slightly beyond the fringe of the support member, a small overlap occurs allowing a gap to permit some air to provide proper ventilation to the ear. When not in use, the ear protective device is small enough to be stored in a small pocket.

I claim:

1. An ear protection device for attachment to support structure for eyeware such as ski goggles or glasses to keep the ear warm and covered without substantially interfering with sound transmission to the ear, said device comprising:

a hinge member having an attached support member and covering member;

said support member including an opening (i) sufficiently large to permit the ear to pass therethrough and (ii) sufficiently small to provide a comfortable fit around the ear when in a mounted position;

said covering member including a shell which provides an exterior enclosure for the ear when the hinged member is in a folded configuration with the support member and covering member in a closed, contiguous relationship and which is fabricated of a material which provides protection against adverse weather.

2. An ear protection device for attachment around lateral support structure for eyeware such as ski goggles or glasses comprising:

a flexible support member having a central opening positioned within the support member for placement at the ear and against a wearer's head and a substantially circumscribing body around the opening having a first side for positioning against the head and a second side disposed away from the head, the circumscribing body having a configuration and sufficient width to extend beyond the circumference of the ear to be covered;

a covering member large enough to provide an exterior enclosure for the ear and fabricated of material which offers protection against cold temperatures and moisture, said covering having an opposing interior surface and exterior face; and means coupled to the support and covering members for joining the second side of the circumscribing body of the support member to the interior surface of the covering member to form an attachment means which permits the respective members to be coupled together in an enclosing relationship with respect to and around the lateral support structure of the eyewear.

3. A device as defined in claim 2, wherein the circumscribing body of the flexible support member comprises an annular body configured to be fitted around and supported by the ear of the wearer.

4. A device as defined in claim 2, wherein the first side of the circumscribing body and the interior surface of the covering member are concave with respect to the wearer's head, the second side and the exterior face respectively being convex, the second side of the support member being configured to nest at the interior surface of the covering member.

5. A device as defined in claim 2, wherein the attachment means for coupling the respective support and covering members together comprises a first sheet of VELCRO material adhered to the interior of the covering member in juxtaposed position to the first sheet, the respective sheets of material being adapted to adhere upon closure of the respective members about the ear.

6. A device as defined in claim 2, wherein the attachment means comprises a hinge member coupled between the respective support member and covering member such that the covering member can be folded into a closed, nested configuration with respect to the second side of the support member.

7. A device as defined in claim 6, wherein the hinge member is formed as an integral part of the support member.

8. A device as defined in claim 6, wherein the support member, the covering member and the hinge member are all formed as a single, integral structure.

9. A device as defined in claim 2, wherein the support member and covering member are constructed sufficiently small to permit storage in a pocket.

10. A device as defined in claim 2, wherein the periphery of the covering member has a forward and rearward indentation forming a channel through which a ski goggle strap can pass and which allows the covering member to close over the strap without being deflected away from a closed position.

11. A device as defined in claim 2, wherein the covering member includes means for mounting an ear speaker used with a tape recorder or radio, said mounting means being coupled to the interior surface at a location suited to position the ear speaker over the ear in listening position.

12. A device as defined in claim 11, wherein the means for mounting the speaker comprises an annular piece of Velcro attached to the interior surface of the covering member with a tooth side exposed toward the ear, said annular piece having a central opening smaller in diameter than the speaker and sufficiently large to provide a recess for a back portion of the speaker, said speaker including a covering adapted for adhering contact in the Velcro.

13. A device as defined in claim 2, further comprising means positioned at a top portion of the device when in a closed configuration for attachment to an arcuate head support band adapted to be secured over the head of the wearer and which includes positioning support means for the device in the absence of lateral support structure of goggles or glasses.

* * * * *